United States Patent [19]

Marken et al.

[11] Patent Number: 5,597,707
[45] Date of Patent: Jan. 28, 1997

[54] TUMOR ASSOCIATED ANTIGEN RECOGNIZED BY THE MURINE MONOCLONAL ANTIBODY L6, ITS OLIGONUCLEOTIDE SEQUENCE AND METHODS FOR THEIR USE

[75] Inventors: John Marken; Gary L. Schieven; Ingegerd Hellstrom; Karl E. Hellstrom, all of Seattle; Alejandro Aruffo, Edmonds, all of Wash.

[73] Assignee: Bristol-Myers Squibb Company, New York, N.Y.

[21] Appl. No.: 48,700

[22] Filed: Apr. 15, 1993

[51] Int. Cl.⁶ .......................... C07H 21/00; C12P 21/06; C12N 15/00; G01N 33/574
[52] U.S. Cl. .................. 435/69.3; 435/7.23; 435/69.1; 435/172.2; 435/172.3; 935/52; 935/55; 536/22.1; 536/23.1
[58] Field of Search .......................... 435/69.3, 69.1, 435/7.23, 172.2, 172.3; 536/23.1, 22.1; 935/52, 55

[56] References Cited

U.S. PATENT DOCUMENTS

| | | |
|---|---|---|
| 4,906,562 | 3/1990 | Hellstrom et al. . |
| 4,935,495 | 6/1990 | Hellstrom et al. . |
| 5,001,230 | 3/1991 | Brown et al. . |

OTHER PUBLICATIONS

Allum et al. (1986) Monoclonal Antibodies in the Diagnosis and Treatment of Malignant Conditions, Surg. Ann. 18:41–64.

DeNardo et al. (1991) Breast Epithelial Antigens, Molecular Biology to Clinical Applications, R. L. Cerciani Editor, Plenum Press, NY pp. 227–232.

Fink et al. (1984) Monoclonal Abs as Diagnostic Reagents for the Identification and Characterization of Human Tumor Antigens, Prog. Clin. Pathol. 9:121–133.

Goodman et al. (1990) Phase I Trial of Murine MAb L6 in Breast, Colon, Ovarian & Lung Cancer, J. Clinical Oncol. 8:1083–1092.

Hellstrom et al. (1986) Monoclonal Mouse Antibodies Raised Against Human Lung Carcinoma, Cancer Res. 46:3917–3923.

Hellstrom et al. (1990) Antitumor Effects of L6, an IgG2a Antibody That Reacts With Most Human Carcinomas, Cancer Res. 50:2183–2190.

Hellstrom et al. (1986) Highly Tumor–reactive, Internalizing, Mouse MAbs to $Le^y$–related Cell Surface Antigens, Proc. Natl. Acad. Sci. USA 83.7059–7063.

Houghton et al. (1986) MAbs: Potential Applications to the Treatment of Cancer, Semin. Oncol. 13:165–179.

Lavie et al. (1989) Evaluation of L6, an Anti–carcinoma Murine MAb in Tumor–bearing Nude Mice, Radiotherapy and Oncol. 15:295–305.

Marken et al. (1992) Cloning & Expression of the Tumor-associated Antigen L6, Proc. Natl. Acad. Sci. USA 89:3503–3507.

Nilaver et al. (1990) Identification of Neurophysin Immunoreactivity in Hypothalamus by a Monoclonal Antibody to a Carcinoma Cell Surface Antigen Neuroendocrinology 51:565–571.

Papsidero (1985) Recent Progress in the Immunological Monitoring of Carcinomas Using MAbs, Sem. Surg. Oncol. 1:171–181.

Rosenbaum et al. (1990) Expression of Neurophysin–related Precursor in Cell Membranes of a Small–cell Lung Carcinoma, Proc. Natl. Acad. Sci. USA 87. 9928–9932.

Scholm et al. (1985) Potential Clinical Utility of MAbs in the Management of Human Carcinomas, in Important Advances in Oncology 1985, J. B. Lippincott Company, Philadelphia, Ch. 9, pp. 170–192.

Sikille et al. 1990. Structure of the Gene of term–transplantation Antigen P198: A point Mutation Generates . . . J. Exp. Med. 172:35–45.

Leung et al. 1978. A Glycoprotein set specifically associated with the surface and cytosal of human breast . . . J. Immunol. 121(4): 1287–1296.

Primary Examiner—James C. Housel
Assistant Examiner—Nita M. Minnifield

[57] ABSTRACT

The present invention definitively identifies and characterizes the tumor-associated antigen immunologically recognized by the murine monoclonal antibody L6. Further, the present invention provides the nucleotide sequence which encodes the L6 antigen. Various diagnostic, prophylactic and therapeutic methods comprising the L6 antigen and the nucleotide sequence which encodes the L6 antigen are also provided.

13 Claims, 6 Drawing Sheets

```
TCGAGATCCATTGTGCTCTAAAGGCTCGCCCTCCTGTGCATCGCGGCTAATTTGGGGTAT  (60)
CACTGAGCTGAAGACAAAGAGAAGGGGGAGAAAACCTAGCAGACCACCATGTGCTATGGG (120)
                                              MetCysTyrGly
                                                         *
    AAGTGTGCACGATGCATCGGACATTCTCTGGTGGGGCTCGCCCTCCTGTGCATCGCGGCT (180)
  5 LysCysAlaArgCysIleGlyHisSerLeuValGlyLeuAlaLeuLeuCysIleAlaAla
        *       *                      I      *
    AATATTTTGCTTTACTTTCCCAATGGGGAAACAAAGTATGCCTCCGAAAACCACCTCAGC (240)
 25 AsnIleLeuLeuTyrPheProAsnGlyGluThrLysTyrAlaSerGluAsnHisLeuSer
    CGCTTCGTGTGGTTCTTTTCTGGCATCGTAGGAGGTGGCCTGCTGATGCTCCTGCCAGCA (300)
 45 ArgPheValTrpPhePheSerGlyIleValGlyGlyGlyLeuLeuMetLeuLeuProAla
                                              II
    TTTGTCTTCATTGGGCTGGAACAGGATGACTGCTGTGGCTGCTGTGGCCATGAAAACTGT (360)
 65 PheValPheIleGlyLeuGluGlnAspAspCysCysGlyCysCysGlyHisGluAsnCys
                         *  *      *  *                      *
    GGCAAACGATGTGCGATGCTTTCTTCTGTATTGGCTGCTCTCATTGGAATTGCAGGATCT (420)
 85 GlyLysArgCysAlaMetLeuSerSerValLeuAlaAlaLeuIleGlyIleAlaGlySer
                  *                              III
    GGCTACTGTGTCATTGTGGCAGCCCTTGGCTTAGCAGAAGGACCACTATGTCTTGATTCC (480)
105 GlyTyrCysValIleValAlaAlaLeuGlyLeuAlaGluGlyProLeuCysLeuAspSer
               *                                    *
    CTCGGCCAGTGGAACTACACCTTTGCCAGCACCGAGGGCCAGTACCTTCTGGATACCTCC (540)
125 LeuGlyGlnTrpAsnTyrThrPheAlaSerThrGluGlyGlnTyrLeuLeuAspThrSer
                       ---CHO---
    ACATGGTCCGAGTGCACTGAACCCAAGCACATTGTGGAATGGAATGTATCTCTGTTTTCT (600)
145 ThrTrpSerGluCysThrGluProLysHisIleValGluTrpAsnValSerLeuPheSer
              *                              ---CHO---
    ATCCTCTTGGCTCTTGGTGGAATTGAATTCATCTTGTGTCTTATTCAAGTAATAAATGGA (660)
165 IleLeuLeuAlaLeuGlyGlyIleGluPheIleLeuCysLeuIleGlnValIleAsnGly
                           IV           *
    GTGCTTGGAGGCATATGTGGCTTTTGCTGCTCTCACCAACAGCAATATGACTGCTAAAAG (720)
185 ValLeuGlyGlyIleCysGlyPheCysCysSerHisGlnGlnGlnTyrAspCysEnd
                 *  *                                 *
    AACCAACCCAGGACAGAGCCACAATCTTCCTCTATTTCATTGTAATTTATATATTTCACT (780)
    TGTATTCATTTGTAAAACTTTGTATTAGTGTAACATACTCCCCACAGTCTACTTTTACAA (840)
    ACGCCTGTAAAGACTGGCATCTTCACAGGATGTCAGTGTTTAAATTTAGTAAACTTCTTT (900)
    TTTGTTTGTTTATTTGTGTAACATACTCCCCACAGTCTACTTTTACAAACGCCTGTAAAG (960)
    ACTGGCATCTTCACAGGATGTCAGTGTTTAAATTTAGTAAACTTCTTTTTTGTTTGTTTA (1020)
    TTTGTTTTTGTTTTTTTTAAGGAATGAGGAAACAAACCACCCTCTGGGGTAGTTTACA   (1080)
    GACTGAGTGACAGTACTCAGTATATCTGAGATAAACTCTATAATGTTTTGGATAAAAATA (1140)
    ACATTCCATGGCACATATATACAATAGTGATTGGCTTTAGAGCACAAT             (1188)
```

Figure 2A

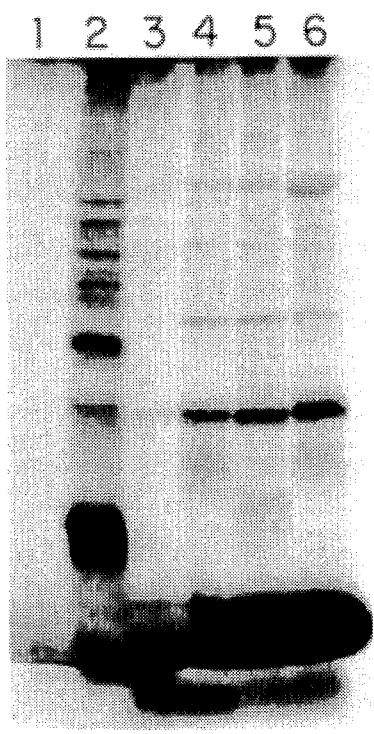
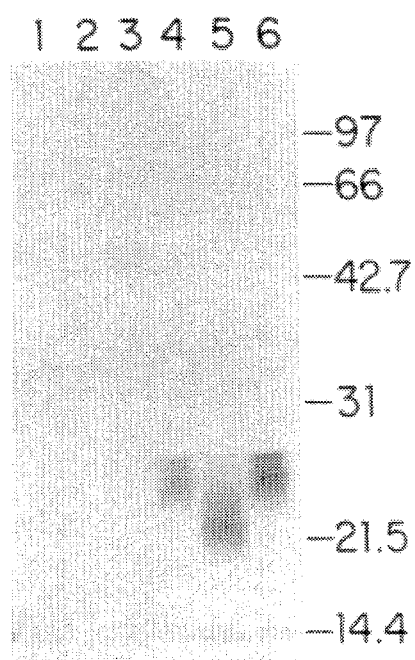
Figure 5A
Figure 5B

TUMOR ASSOCIATED ANTIGEN RECOGNIZED BY THE MURINE MONOCLONAL ANTIBODY L6, ITS OLIGONUCLEOTIDE SEQUENCE AND METHODS FOR THEIR USE

FIELD OF INVENTION

The present invention relates to an isolated and substantially purified glycoprotein tumor-associated antigen immunologically recognized by the murine monoclonal antibody L6. The present invention further relates to an oligonucleotide sequence which encodes the glycoprotein tumor-associated antigen immunologically recognized by L6. Methods for the use of both the glycoprotein and the oligonucleotide sequence are also encompassed by the present invention. Such methods include diagnostic, prophylactic and therapeutic methods comprising the use of the purified glycoprotein tumor-associated antigen or the oligonucleotide sequence encoding the antigen.

BACKGROUND OF THE INVENTION

In recent years many monoclonal antibodies immunologically reactive with tumor-associated antigens have been isolated (see, e.g., Papsidero, 1985, Sem. Surg. Oncol. 1: 171–81; Scholm et al. 1985 in *Important Advances in Oncology*, pages 170–192; Allum et al., 1986, Surg. Ann. 18: 41064; and Houghton et al., 1986, Semin. Oncol. 13: 165–179). The antigens bound by these monoclonal antibodies and characterization of the binding pattern of the monoclonal antibodies in most cases are incomplete and somewhat uncertain. Although a few have been completely characterized. Some of the more completely characterized monoclonal antibodies have been found to bind to a variety of tumor-associated antigens including glycoproteins, glycolipids and mucins (see, e.g., Fink et al., 1984, Prog. Clin. Pathol. 9: 121–133).

Murine monoclonal antibody L6 was raised against a human lung adenocarcinoma (Hellstrom et al., 1986, Cancer Res. 46: 3917–3923; Hellstrom et al., 1986, Proc. Natl. Acad. Sci. USA. 83: 7059–7063; U.S. Pat. No. 4,906,562; U.S. Pat. No. 4,935,495; and U.S. Pat. No. 5,091,177). In the initial effort to characterize the epitope to which monoclonal antibody L6 bound it was found that a glycolipid antigen, which in purified form had a terminal carbohydrate structure;

as determined by solid phase ELISA and immunoblot of standard defined glycolipid structures separated by thin layer chromotography was recognized. Additionally, when L6 was used in radioimmune precipitation analysis of disrupted minor cells an unknown protein antigen of 20,000 dalton molecular weight was precipitated among others.

In later studies, L6 was found to stain intra-cytoplasmic material within the magnocellular component of the hypothalamoneuropophysial system. Further evaluation of this observation lead to the conclusion that L6 was binding to proneurophysin (Nilaver et al., 1990, Neuroendocrinology 51: 565–571 and Rosenbaum et al., 1990, Proc. Natl. Acad. Sci. USA 87: 9928–9932). A definitive characterization of the anitgen bound by L6 has been elusive and to date contradicting and so inconclusive that the antigen to which monoclonal antibody L6 binds is unknown.

Functionally, monoclonal antibody L6, an Ig G2a, has been found to mediate antibody-dependent cellular cytotoxicity (ADCC) with human mononuclear cells and complement-dependent cytotoxicity (CDC) with human complement. The antibody also has been found to localize to antigen-positive human tumor cells in nude mice (Lavie et al., 1989, Radiotherapy and Oncol. 15: 245–305) and inhbit their outgrowth (Hellstrom et al., 1986, Proc. Natl. Acad. Sci. USA 83: 7059–7063). Because the L6 antigen appears to be highly expressed on tumor cells and apparently expressed at a low level, or not at all, on most normal cell types monoclonal antibody L6 has been tried in several limited clinical studies. A phase I clinical study carried out in patients with recurrent cancer of either breast, colon, lung or ovary demonstrated that murine monoclonal antibody L6 was well tolerated and effectively localized to tumor in vivo and that one patient, with recurrent breast cancer on the chest wall, underwent complete, although temporary, remission (Goodman et al., 1990, J. Clinical Oncol. 8: 1083–1092). In other clinical studies, radiolabelled murine and chimeric (mouse-human) L6 antibodies were shown to deliver sufficient amounts of radioactivity to tumors to be of therapeutic interest (DeNardo et al., 1991, in *Breast Epithelial Antigens*, ed. R. L. Ceriani, Plenum Press, New York, pp. 227–232).

Although the clinical potential of monoclonal antibodies and various chimeras specific for the L6 antigen have been established, the definitive identification of the cell-surface tumor-associated antigen recognized by L6 has remained elusive. Definitive characterization of the antigen would provide insite not only into what the tumor-associated antigen may be, but also supply a reagent for use in enhancing a more specific productive immune response to a tumor.

SUMMARY OF THE INVENTION

The present invention is directed to an isolated and substantially purified glycoprotein tumor-associated antigen. The antigen is immunologically specifically recognized by the murine monoclonal antibody L6 and its derivatives, fragments and chimeras. The present invention further relates to an isolated oligonucleotide molecule comprising a nucleotide sequence which encodes the L6 tumor-associated antigen.

Methods for the use of both the purified glycoprotein L6 antigen and the isolated oligonucleotide encoding the L6 antigen are also disclosed. Such methods include diagnostic, prophylactic and therapeutic methods, as well as methods to recombinantly express the L6 antigen in prokaryotic or eukaryotic host cells. The present invention also provides for therapeutic compositions and for diagnostic kits comprising the isolated L6 antigen and purified oligonucleotide encoding L6 antigen.

BRIEF DESCRIPTION OF THE FIGURES

FIG. 2A: Nucleotide sequence of the cDNA obtained from the H3347 cDNA library encoding the L6 antigen is provided. Nucleotide numbering is given in parentheses at right, and amino acid numbering is given at the left. The location of the potential N-linked glycosylation sites are shown (CHO), and the four putative hydrophobic transmembrane domain are underlined and labeled I through IV. Cysteine residues are highlighted (*) and the presumed polyadenylation signals are double underlined.

FIG. 5: L6 antigen transcribed and translated in vitro. Autoradiographs of $^{35}$S-cysteine labeled, SDS-PAGE-separated products of in vitro-translated mRNA from cDNA encoding the L6 antigen are shown directly (A) or immunoprecipitated with chimeric L6 (B). Lane 1, without RNA or microsomal membranes; Lane 2, with RNA, no membranes; Lane 3, with membranes, no RNA; Lane 4, L6 antigen RNA and microsomal membranes; Lane 5, same as Lane 4, but treated with N-glycanase; Lane 6, same as Lane 4, but treated with O-glycanase and neuraminidase.

DESCRIPTION OF PREFERRED EMBODIMENTS

Figure 1:
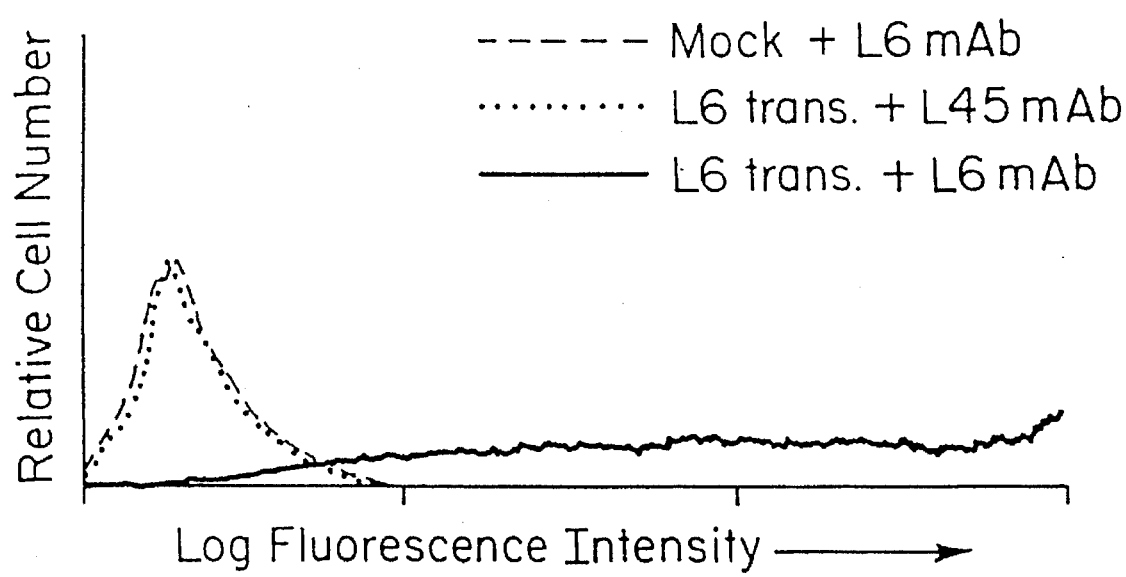
FIG. 1: L6 transfected COS cells were either mock transfected or transfected with a cDNA clone encoding the L6 antigen, stained with either anti-L6 monoclonal antibody, L6, or an isotype matched control, L45, followed by FITC-conjugated anti-mouse Ig second step reagent. A total of 10,000 cells were analyzed by FACS.

The present invention is directed to an isolated and substantially purified tumor-associated antigen, and its murine analog. In particular, the antigen is that recognized by the murine monoclonal antibody L6 (ATCC HB 8677, U.S. Pat. Nos. 4,906,562; 4,935,495 and 5,091,177, incorporated herein by reference). The present invention is further directed to methods for the production of the L6 antigen by conventional or recombinant DNA technology and to therapeutic and diagnostic methods utilizing the L6 antigen.

Human L6 antigen is an integral membrane protein with a predicted molecular mass of approximately 22 kDA. The cDNA encoding the L6 antigen is 1188 base pairs (bps) long and is predicted to encode a protein of 202 amino acid residues. Analysis of the putative amino acid sequence predicted from cDNA made from mRNA isolated from human colon carcinoma cell line H3347 (Hellstrom et al., 1990, Cancer Res. 50: 2183–2190) by hydrophilicity indicates that human L6 antigen is integral to the cell membrane spanning the membrane four times. Its lack of an amino-terminus hydrophobic domain further suggests a membrane orientation in which both the amino-terminal and carboxyl-terminal ends of the protein are cytoplasmic. Orientation of the L6 antigen in the membrane as described would give rise to two hydrophilic extracellular domains, one between the first and second hydrophobic domains, the other between the third and fourth hydrophobic domains.

Composition of the putative amino acid sequence of the L6 antigen with the reported amino acid sequence of other proteins indicates that the L6 antigen is structurally similar to a large family of integral membrane proteins, which include the leukocyte antigens CD9, CD37, CD53, CD63 (ME491) and TAPA-1, the carcinoma associated antigen CO-029 and the Schistoma manoni worm antigen 8M23. All of the proteins in this family would appear from their amino acid sequences to share a similar structure and orientation within the plasma membrane. Like the L6 antigen, the members of this family of proteins are rich in cysteine residues and many of the positions within the molecular structures where the cysteine residues are found are highly conserved by all of the proteins within the family.

Because of the presence of the L6 antigen on lung, breast, colon and ovarian carcinoma cells, this protein is an attractive target for therapeutic intervention and for diagnostic methods. Furthermore, availability of cDNA encoding the L6 antigen will allow further definition of the role of L6 antigen in the genesis of carcinomas, in particular, comparisons between the L6 gene in normal and neoplastic cells.

Construction of cDNA or Genomic Libraries

Messenger RNA (mRNA) for the original characterization of the L6 antigen or for future production of the L6 antigen, or its analogs can be obtained from cell sources that express the L6 antigen, whereas genomic sequences for L6 antigen may be obtained from any cell source. For example, cells of the human colon carcinoma line H3347 can be utilized either for the source of mRNA, or to provide genomic sequences, which encode the L6 antigen.

Either cDNA or genomic libraries can be prepared from various sources using techniques well known in the art. For example, the DNA fragments can be inserted into a plasmid capable of replication in both prokaryotic and eukaryotic cells. The plasmids, containing the DNA fragments can then be amplified by transfecting a prokaryotic host cell. After amplification the plasmids are then isolated from the prokaryotic host cell and used to transfect a eukaryotic host cell, i.e., COS cells (Gerard and Glugman, 1986, Mol. Cell Biol. 6(12): 4570–4577). Any membrane proteins encoded by a DNA fragment from the cDNA or genomic DNA library are transiently expressed on the surface of the transfected cells.

The presence of the cell membrane protein can be detected by monoclonal antibody panning. Cells transfected with the cDNA or genomic DNA fragments are grown for a period of time sufficient for expression of the L6 antigen on the surface of the eukaryotic host cell. Monoclonal antibodies specific for the L6 antigen can be used to select those transfected cells which express a cell surface protein capable of immunologically reacting with the monoclonal antibodies. Plasmid DNA is recovered from the L6 antibody binding cells and can be used to transform a prokaryotic host cell for amplification as previously described. Several rounds of panning can be required to isolate a single DNA fragment encoding the L6 antigen. The DNA fragment obtained can then be further analyzed to determine nucleotide sequence, putative amino acid sequence and other characteristics of the L6 antigen by methods well known to the skilled artisan. The DNA fragment encoding the L6 antigen can also be used to transfect other eukaryotic cell lines which express transfected DNA sequences in a non-transient manner, chinese hamster ovary cells are such a cell line. L6 antigen expressed by the transfected host cell can be used for further characterization, well known to the skill artisan, or used to produce quantities of L6 antigen.

Production of L6 Antigen By Recombinant DNA Technology

Fragments of cDNA or genomic DNA from various types of cells to form a library can be obtained as described above. The fragments which encode the L6 antigen can be identified by screening such libraries with a nucleotide probe homologous to a portion of the L6 antigen sequence (Sequence Listing I.D. No. 1). Although portions of the coding sequence may be utilized for cloning and expression, full length clones, i.e., those containing the entire coding region for L6 antigen, are preferable for expression. Techniques are well known to the skilled artisan for the isolation of DNA, generation of appropriate restriction fragments, construction of clones and libraries, and screening of recombinants. See, for example, the techniques described in *Molecular Cloning: A Laboratory Manual*, 2d Ed., J. Seabrook, E. F. Futsch and T. Maniatis, Cold Spring Harbor Laboratory Press, 1989, (incorporated herein by reference).

Regardless of the method chosen to identify and clone the L6 antigen coding sequence, expression cloning methods can be utilized to substantially reduce the screening effort. Recently, a one step procedure for cloning and expressing antibody genes has been reported (McDafferty et al., 1990, Nature 348: 552–554; Winter and Milstein, 1991, Nature 349: 293–299). Based on this technology, the L6 gene can likewise be cloned directly into a vector at a site adjacent to the coat protein gene of a bacteriophage, such as lambda or fd. The phage carrying the L6 antigen gene expresses the fusion protein on its surface so that columns containing an L6 antigen-specific antibody can be used to select and isolate phage particles with binding activity. Transient gene expression systems can also be utilized to identify the correct L6 antigen gene as described above.

Due to degeneracy of the nucleotide coding sequences, other DNA sequences which encode analogous amino acid sequences for any known L6 antigen gene can be used in the practice of the present invention for cloning and expression of L6 antigens. Such alterations include deletions, additions, or substitutions of different nucleotide residues resulting in a DNA sequence that encodes the same or a functionally equivalent gene product. The gene product can contain deletions, additions or substitutions of amino acid residues within the amino acid sequence, which result in a silent change thus producing a bioactive product. Such amino acid substitutions may be made on the basis of similarity in polarity, charge, solubility, hydrophobicity, hydrophilicity and/or amphipathic nature of the residues involved. For example, negatively charged amino acids include aspartic acid and glutamic acid; positively charged amino acids include lysine and arginine; amino acids with uncharged amino acids include lysine and arginine; amino acids with uncharged polar head groups having similar hydrophilicity values include the following: leucine, isoleucine, valine, glycine, alanine, asparagine, glutamine, serine, threonine, phenylalanine, and tyrosine.

In order to express a biolgically active L6 antigen, the nucleotide sequence encoding L6 antigen, or a functionally equivalent nucleotide sequence, is inserted into an approproate expression vector, i.e., a vector which contains the necessary elements for the transcription and translation of the inserted coding sequence. Modified versions of the L6 antigen coding sequence can be engineered to enhance stability, production, purification or yield of the expressed product. For example, the expression of a fusion protein or a cleavable fusion protein comprising L6 antigen and a heterologous protein can be engineered. Such a fusion protein can be readily isolated by affinity chromatography; e.g., by immobilization of a column binding protein specific for the heterologous protein. Where a cleavage site is engineered between the L6 antigen moiety and the heterologous protein, the L6 antigen can be released from the chromatographic column by treatment wiht an appropriate enzyme or agent that disrupts the cleavage site (e.g., see Booth et al., 1988, Immunol. Lett. 19: 65–70; and Gardella et al., 1990, J. Biol. Chem. 265: 15854–15859).

Methods which are well known to those skilled in the art can be used to construct expression vectors containing the L6 antigen coding sequence and appropriate transcriptional/translational control signals. These methods include in vitro recombinant DNA techniques, synthetic techniques, and in vivo recombinant/genetic techniques. See, for example, the techniques described in *Molecular Cloning: A Laboratory Manual*, 2d Ed., J. Seabrook, E. F. Futsch and T. Maniatis, Cold Spring Harbor Laboratory Press, 1989, (incorporated herein by reference).

A variety of host-expression vector systems may be utilized to express the L6 antigen coding sequence. These include but are not limited to microorganisms such as bacteria transformed with recombinant bacteriophage DNA, plasmid DNA or cosmid DNA expression vectors containing the L6 antigen coding sequence; yeast transformed with recombinant yeast expression vectors containing the L6 antigen coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the L6 antigen coding sequence; insect cell systems infected with recombinant virus expression vectors (e.g., baculovirus) containing the L6 antigen coding sequence; or animal cell systems infected with recombinant virus expression vectors (e.g., retroviruses, adenovirus, vaccinia virus) containing the L6 antigen coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. can be used in the expression vector (see e.g., Bitter et al., 1987, Methods of Enzymology 153: 516–544). For example, when cloning in bacterial systems, inducible promoters such as pL of bacteriphage λ, plac, ptrp, ptac (ptrp-lac hybrid promoter) and the like can be used. When cloning in mammalian cell systems, promoters derived from the genome of mammalian cells (e.g. metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques can also be used to provide for transcription of the inserted L6 antigen coding sequence.

In bacterial systems a number of expression vectors can be advantageously selected depending upon the use intended for the L6 antigen expressed. For example, when large quantities of unglycosylated L6 antigen are to be produced, vectors which directed the expression of high levels of fusion protein products that are readily purified may be desirable. Those which are engineered to contain a cleavage site to aid in recovering L6 antigen are preferred. Such vectors include but are not limited to the *E. coli* expression vector pUR278 (Ruther et al., 1983, EMBO J. 2: 1791), in which the L6 antigen coding sequence may be ligated into the vector in frame with the lac Z coding region so that a hybrid L6 antigen-lac Z protein is produced; pIN vectors (Inouye & Inouye, 1985, Nucleic Acids Res. 13: 3101–3109; Van Heeke & Schuster, 1989, J. Biol. Chem. 264: 5503–5509); and the like.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, *Expression and Secretion Vectors for Yeast*, in Acad. Press, N.Y., Vol. 153, pp. 516–544; Glover, 1986 *DNA Cloning*, Vol. II, IRL Press, Wash., D.C., Ch. 3; and Bitter, 1987, Heterologous Gene Expression in Yeast, *Methods in Enzymology*, Eds. Berger & Kimmel, Acad. Press, N.Y., Vol. 152, pp. 673–684; and *The Molecular Biology of the Yeast Saccaromyces*, 1982, Eds. Strathern et al., Cold Spring Harbor Laboratory Press, Vols. I and II. A constitutive yeast promoter such as ADH or LEU2 or an inducible promoter such as GAL may be used (Cloning in Yeast, Ch. 3, R. Rothstein In: *DNA Cloning* Vol. 11, A Practical Approach, Ed. DM. Glover, 1986, IRL Press, Wash., D.C.). Alternatively, vectors may be used which promote integration of foreign DNA sequences into the yeast chromosome.

In cases where plant expression vectors are used, the expression of the L6 antigen coding sequence may be driven by any of a number of promoters. For example, viral promoters such as the 35S RNA and 19S RNA promoters of CaMV (Brisson et al., 1984, Nature 310: 511–514), or the coat protein promoter to TMV (Takamatsu et al., 1987, EMBO J. 6: 307–311) may be used; alternatively, plant promoters such as the small subunit of RUBISCO (Coruzzi et al., 1984, EMBO J. 3: 1671–1680; Broglie et al., 1984, Science 224: 838–843); or heat shock promoters, e.g., soybean hsp17.5-E or hsp17.3-B (Guffey et al., 1986, Mol. Cell. Biol. 6: 559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology,* Academic Press, N.Y., Section VIII, pp. 421–463; and Grierson & Corey, 1988, *Plant Molecular Biology,* 2d Ed., Blackie, London, Ch. 7–9.

An alternative expression system which could be used to express L6 antigen is an insect system. In one such system, *Autographa californica* nuclear polyhedrosis virus (AcNPV) is used as a vector to express foreign genes. The virus grows in *Spodoptera frugiperda* cells. The L6 antigen coding sequence can be cloned into non-essential regions (for example the polyhedrin gene) of the virus and placed under control of an AcNPV promoter (for example the polyhedrin promoter). Successful insertion of the L6 antigen coding seqeunce will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. E.g., see Smith et al., 1983, J. Viol. 46: 584; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of L6 antigen. Mammalian cell lines may be preferable. Such host cell lines may include but are not limited to CHO, VERO, BHK, HeLa, COS, MDCK, −293, and WI38.

Mammalian cell systems which utilize recombinant viruses or viral elements to direct expression may be engineered. For example, when using adenovirus expression vectors, the L6 antigen coding sequence my be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region El or E3) will result in a recombinant virus that is viable and capable of expressing the L6 antigen in infected hosts (e.g. see Logan & Shenk, 1984, Proc. Natl. Acad. Sci. USA 81: 3655–3659). Alternatively, the vaccinia virus 7.5K promoter may be used. (e.g., see, Mackett et al., 1982, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell Biol. 1: 486). Shortly after entry of this DNA into mouse cells, the plasmid replicates to about 100 to 200 copies per cell. Transcription of the inserted cDNA does not require integration of the the plasmid into the host's chromosome, thereby yielding a high level of expression. These vectors can be used for stable expression by includng a selectable marker in the plasmid, such as, for example, the neogene. Alternatively, the retroviral genome can be modified for use as a vector capable of introducing and directing the expression of the L6 antigen gene in host cells (Cone & Mulligan, 1984, Proc. Natl. Acad. Sci. USA 81: 6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the L6 antigen cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limted to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in $tk^-$, $hgprt^-$ or $aprt^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin, et al., 1981, J. Mol. Biol. 1510: 1); and hygro, which confers resistance to hygromycin (Santerre, et al., 1984, Gene 30: 147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (omithine decarboxylase) which confers resistance to the omithine decarboxylase inhibitor, 2-(difluoromethyl)-DL-omithine, DFMO (McConlogue L., 1987, in: *Current Communications in Molecular Biology*, Cold Sprig Harbor Laboratory ed.).

Chemical Synthetic Methods

The L6 antigen can also be produced in whole or in part by solid phase chemical synthetic tehcniques based on the amino acid sequence disclosed herein (see Crieghton, 1983, *Proteins Structures and Molecular Principles*, W.H. Freeman and Co., N.Y. pp. 50–60; Stewart and Yound, 1984, *Peptide Synthesis*, 2nd ed., Pierce Chemical Co.). This approach may be particularly useful in generating specific domains of L6 antigen corresponding to one or more of its biologically active regions. Peptides corresponding to various amino acid sequences within domains predicted to be oriented outward from the cell membrane can be synthesized and used to induce polyclonal and monoclonal antibodies in a selected animal.

Antibody Production

Also within the scope of the invention is the production of polyclonal and monoclonal antibodies which recognize specific domains of the L6 antigen or related proteins.

Various procedures known in the art may be used for the production of polyclonal antibodies to epitopes of L6 antigen. For the production of antibodies, various host animals can be immunized by injection with the L6 antigen protein, or an L6 peptide, including but not limited to rabbits, hamsters, mice, rats, ets. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium paryum*.

A monoclonal antibody to a domain of the L6 antigen, oriented outward from the cell membrane, may be prepared using any technique which provides for the production of antibody molecules by continuous cell lines in culture. These include but are not limited to the hybridoma originally described by Kohler and Milstein (1975, Nature 256: 495–597), and the more recent human B-cell hybridoma technique (Kosbor et al., 1983, Immunology Today 4: 72) and EBV-hybridoma technique (Cole et al., 1985, *Monoclonal Antibodies and Cancer Therapy*, Alan R. Liss, Inc., pp. 77–96).

Antibody fragments which contain the idiotype of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Antibodies to L6 antigen find use in the qualitative and quantitative detection of L6 antigen and its homologs, in the affinity purification of L6 antigen, and in the elucidation of L6 antigen biosynthesis, metabolism and function. Antibodies to L6 antigen may also be useful as diagnostic and therapeutic agents.

Uses of L6 Antigen and Purified Oligonucleotides Encoding L6 Antigen

L6 antigen has now been fully elucidated. Purified L6 antigen, here defined as the entire polypeptide or immunologically equivalent fragments, can find use in many diagnostic, prophylactic and therapeutic methods. Diagnostic methods can include, for example, the determination of the presence of a malignant condition based on an immune response developed against the L6 antigen. The term "malignant condition" refers to the presence of neoplastic, malignant or tumor cells, or the like. Enzyme Linked Immunospecific Assays can be designed which use the purified L6 antigen to capture antibodies specific to the L6 antigen Various formats for these types of assays are numerous and well known to those skilled in the art. Generally, a diagnostic kit can be assembled which comprises (a) purified L6 antigen, and (b) an antibody specific for human immunoglobulin molecules and a label for detecting bound antibody. The reagents can also include ancillary agents such as buffering agents and protein stabilizing agents, e.g., polysaccharides and the like. The diagnostic kit can further comprise, where necessary, other components of a signal-producing system including agents for reducing background interference, control reagents, an apparatus for conducting a test, etc. Many other formats of diagnostic tests are well known in the art and are considered part of the present invention.

The purified L6 antigen of the present invention can also be used in pharmaceutical compositions in prophylactic or therapeutic methods. Preferably, the pharmaceutical compositions may be administered parenterally, i.e., subcutaneously, intramuscularly or intravenously. Thus, the present invention provides compositions for parenteral administration which comprise a solution of the purified L6 antigen dissolved in an acceptable carrier, preferably an aqueous carrier. A variety of aqueous carriers are known and can be used, e.g., water, buffered water, various concentrations of saline, glycine and the like. Auxiliary substances can also be added as required to approximate physiological conditions such as pH adjusting and buffering agents, toxicity adjusting agents and the like, for example, sodium acetate, sodium chloride, potassium chloride, calcium chloride, sodium lactate, etc. Typically, pharmaceutical compositions for prophylactic or therapeutic use will also include a suitable adjuvent, which can include, but are not limited to mineral gels (aluminum hydroxide), surface active substances such as lysolecithin, pluronic polyols, polyanions, peptides, oil emulsions, BCG Coacille Calmette-Guerin) and cornybacterium parvum.

The compositions containing the purified L6 antigen can be administered for prophylactic or therapeutic treatment of malignant conditions. In therapeutic applications, compositions are administered to a patient already known to have a malignant condition, in an amount sufficient to boost the patients immune response to cure or at least partially arrest the speed or growth of the malignancy. An amount adequate to accomplish this is defined as a "therapeutically effective dose". Amounts effective for this use will depend on the severity of the condition and the general state of the patient's own immune system.

In prophylactic applications, compositions of the present invention containing L6 antigen are administered to a patient not already afflicted with a malignant condition, but who may be susceptible to develop a malignancy. The goal of using compositions of the present invention prophylactically is to enhance the patient's resistance to, and ability to destroy, malignant cells as they appear. An amount necessary to enhance the immune response is defined to be a "prophylactically effective dose". In this use, the precise amounts again depend on the patient's state of health.

Single or multiple administrations of the compositions can be carried out with dose levels and pattern of administration being selected by the treating physician. In any event, the pharmaceutical composition should provide a quantity of L6 antigen sufficient to effectively treat the patient.

Purified oligonucleotides of the present invention can be used in the production of L6 antigen, or immunologically equivalent fragments, by recombinant means as described above, or they can be used in various diagnostic methods. Such methods can include assays for mRNA encoding L6 antigen produced by suspect cells or tissues removed from a patient during surgery or in a biopsy. The appearance of mRNA encoding the L6 antigen may be an early indication of transition to a malignant condition. Methods and diagnostic kit formats to quantitate mRNA are well known to the skilled artisan.

The following experimental data and information are offered by way of Examples and are not to be construed as limitations to the scope of the present invention.

EXAMPLE 1

The following example describes the molecular cloning and expression of a cDNA clone which encodes human L6 antigen and the transient expression of the encoded antigen.

RNA Preparation

Human colon carcinoma cell line H3347 (Hellstrom et al., 1990, Cancer Res. 50: 2183–2190) was used for the preparation of mRNA. Cells ($1\times10^9$) were digested with 200 μg/ml proteinase K in 0.5% SDS, 0.1M NaCl, 20 mM Tris, pH 7.5, 10 mM EDTA for one hour at 37° C. Poly-A RNA was extracted with 1 ml oligo-dT sepharose beads after adjustment of the NaCl concentration to 0.5M. The beads were washed by centrifugation with High Salt Buffer (HSB, 0.5 m NaCl, 1 mM EDTA, 0.1% SDS). The mRNA was eluted from the oligo-dT beads with 5 ml of Low Salt Buffer (LSB, 0.1M NaCl, 0.05% SDS, 1 mM EDTA). The eluate was passed over a 1 ml bed volume oligo-dT column equilibrated with HSB and the column was washed with additional column volumes of HSB. Elution of the mRNA was carried out with 3 ml of LSB. RNA was precipitated from the eluate with 0.5M NaCl and 3 volumes of ethanol. After centrifugation to collect the precipitated mRNA the RNA pellet was resuspended in 100 μl of RNase free water.

cDNA Synthesis

Twenty micrograms of the H3347 mRNA was boiled for 30 seconds and cooled on ice. First strand cDNA synthesis was performed in a buffer containing 50 mM Tris, pH 8.8, 50 mM KCl, 6 mM $MgCl_2$, 0.7 units/μl of buffer containing 0.1M Tris, pH 7.5, 25 mM $MgCl_2$, 0.5M KCl, 0.25 mg/ml BSA, and 50 mM DTr, plus 5 μl of DNA polymerase A (5 U/μl) and 2 μl of RNase H (2 U/μl). The reaction was carried out for one hour at 16° C. and then for an additional hour at 22° C. Extraction of double stranded cDNA was with phenol and precipitation was carried out with 0.5M NaCl and three volumes of ethanol. DNA was collected by centrifugation for 5 minutes and the pellet was washed in 70% ethanol and resuspended in 84 μl of Tris EDTA buffer.

Adaptor Ligation and Size Fractionation

Non-palindromic Bst XI adaptors were ligated to the collected cDNA by adding 7.2 μg of 12 mer Bst XI oligo DNA and 7 μg of 9 mer Bst XI oligo DNA adaptors and 2 Weiss units of T4 DNA ligase in 1× ligase buffer (Boehringer Mannheim) in a 100 μl reaction at 16° C. for 18 hours.

The resultant mixture of cDNA was fractionated on a 5 ml potassium acetate gradient (5% to 20%) at 50,000 rpm for 3 hours in a SW 55-ti rotor to isolate cDNA having the appropriate adaptor sequences. Aliquots of 0.5 ml were removed for analysis of fragment size by precipitation with 3 volumes of ethanol and 10 μg of linear polyacrylamide. The preciptated DNA was analyzed on an agarose gel and the fractions corresponding to the aliquots containing DNA fragments with a size greater than 1,200 base pairs were pooled and used for construction of the library.

Library Construction and Amplification

Pooled fractions containing DNA greater than 1,200 base pairs in length were mixed with 2–5 μg of CDM8 plasmid previously cut with Bst XI restriction enzyme in 200 μl containing 0.1 mM ATP, 2 mM dithiotreatol (DTT), 0.1 mg/ml Bovine Serum Albumin (BSA), 1 mM Spermidine and 1 Weiss unit total of T4 DNA ligase at 16° C. for 18 hours. After completion of the incubation *E. coli* in 10 sets of 300 μl plated at 100,000 colonies per plate on ten 22 cm×22 cm Lb agar plates with 25 μl/ml ampicillin and 15 μg/ml tetracycline. After incubation at 37° C. overnight, the colonies were scrapped into Lb broth plus antibiotics as above. Plasmid DNA was prepared from three quarters of the bacteria by the cessium chloride method to form the H3347 cDNA library.

H3347 cDNA Library Screening

Ten plates of 90% confluent COS cells were transfected with the H3347 cDNA library by incubation with 5 ml each Dulbecco's Modified Eagle's Medium, 10% NuSerum, 2 mg/ml H3347 cDNA library plasmid DNA, 400 μg/ml DEA/Dextran, and 50 μg chloroquine phosphate at 37° C. After four hours the media was removed and the cells were incubated with phosphate buffered saline (PBS) with 10% dimethyl sulfoxide (DMSO) for two minutes. The PBS was removed and the cells were allowed to grow for twenty-four hours in DMEM with 10% fetal bovine serum (FBS). After twenty-four hours the cells were replated using trypsin/EDTA and grown for an additional twenty-four hours in DMEM with 10% FBS.

The transfected COS cells were lifted from the plates with PBS containing 0.5 mM EDTA and 0.02% sodium azide and centrifuged at 1000× g for 5 minutes. The cells were resuspended in PBS containing 0.5 mM EDTA, 0.02% sodium azide and 5% FBS. Murine monoclonal antibodies L6 and L6B (which binds to L6 antigen, but does not compete for immunospecific binding with L6) were added to a final concentration of 10 μg/ml and incubated for 30 minutes on ice. The cells were centrifuged through PBS buffer containing 2% Ficol at 200× g for 5 minutes to remove excess unbound antibody and suspended in 2 ml of PBS, 0.5 mM EDTA and 0.02% sodium azide. The cells were added to four petri dishes previously coated with goat anti-mouse IgG containing 3 ml 0.5 mM EDTA, 0.02% sodium azide and 5% FBS. Following incubation at room temperature for two hours the unadherent cells were washed from the plates with PBS, 0.5 mM EDTA and 0.02% sodium azide. Plasmid DNA was collected from the adherent cells by the method of Hirt (J. Mol. Biol., 1967, 26: 365–369) and transformed into competent *E. coli* MC1061/p3 by electroporation to amplify the selected plasmids containing those cDNA fragments which may contain a gene encoding at least a portion of the L6 antigen.

After amplification, approximately 100,000 bacterial colonies were obtained and used to transfect COS cells by protoplast fusion.. After 48 hours of incubation as described above, the panning procedure with L6 monoclonal antibodies and plates coated with goat anti-mouse IgG was repeated for three additional rounds. DNA was extracted from the final pool of transformed bacteria and used to transfect COS cells by the DEA/dextran method described above. The transfected COS cells and were analyzed for L6 antigen expression.

Analysis of L6 Antigen Expression

COS cells at 50% confluence in a 6-cm petri dish were either mock transfected or transfected with one-fifth the DNA obtained from eighteen individual E. coli colonies obtained above. Twelve hours post-transfection the cells were trypsinized and passaged onto fresh dishes as described above. Eighteen to twenty-four hours later 1 µg/ml murine monoclonal antibodies L6 and L6B were added to the cells, incubated for 30 minutes at room temperature and washed twice with PBS.

The washed cells were then incubated for thirty minutes with FITC-conjugated goat anti-mouse IgG antibody (1 µg/ml, Tago) and washed twice with PBS. COS cells transfected by DNA isolated from each of the eighteen bacterial clones obtained after panning were examined by fluorescence microscopy (Nikon).

In another fluorescence analysis for L6 antigen expression mock transfected and transfected COS cells were obtained as above. After passage onto fresh dishes the cells were lifted from the dishes with PBS/EDTA, washed with PBS, 0.5 mM EDTA with 5% FBSI, and resuspended in 1 ml of PBS 0.5 mM EDTA and 5% FBS with 10 µg of L6 monoclonal antibody or an isotype matched monoclonal antibody (L45, IgG2a) as a control. After 1 hour incubation on ice the cells were washed twice with PBS, 0.5 mM EDTA with 5% FBS and resuspended in 500 µl of the same buffer containing 1 µg/ml of fluorescein conjugated goat anti-mouse IgG antibody. The cells were incubated for one hour on ice and then washed twice with PBS, EDTA prior to analysis by Fluorescent Activated Cell Sorter (FACS, EPICS, C, Coulter). See FIG. 1. Two of the eighteen bacterial colonies were determined to contain cDNA which encoded a molecule immunoreactive by fluorescence analysis with both L6 and L6B, but not the control antibody. Further analysis of the cDNA demonstrated that the two bacterial clones contained identical 1.2 kb inserts by preliminary sequence and restriction enzyme analysis; one clone was further characterized.

EXAMPLE 2

Figure 2B:
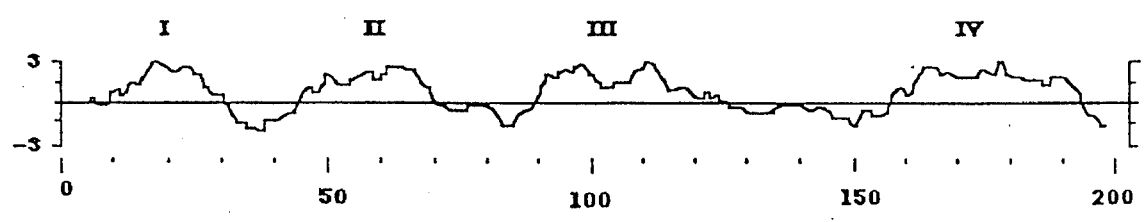
FIG. 2B: Hydrophobicity/hydrophilicity profile determined for the putative amino acid sequence of the L6 antigen.

Characterization and Sequence Analysis of L6 cDNA and Biochemical Characterization of the L6 Antigen Characterization and Sequence Analysis of L6 Antigen cDNA The L6 antigen containing cDNA insert was subcloned in both orientations into M13mp19 (Viera and Messing, 1982, Gene 19: 259–268) and the nucleotide sequence was determined by the dideoxynucleotide method (Sanger et al., 1977, Proc. Natl. Acad. Sci. USA 74: 5463–5467). L6 antigen DNA was found to be 1188 base pairs in length encoding a long open reading frame of 202 amino acid residues (FIG. 2A). The putative protein has a predicted molecular weight of approximately 22 kDa and has the typical features of an integral membrane protein. Examination of the putative amino acid sequence reveals four hydrophobic segments with one long enough to span the plasma membrane one (FIG. 2B). Three of the hydrophobic regions are proximal to the amino terminus and the fourth is located proximal to the carboxy terminus. Hydrophobic domains III and IV are separated by a 29 amino acid long hydrophilic domain which contains two potential N-linked glycosylation sites (Asn-X-Ser/Thr). The L6 antigen is cysteine rich, containing eighteen cysteine residues. The ATG codon which initiates the long open reading frame encoding the L6 antigen is contained within the nucleotide sequence CCAC-CATGT which closely resembles the consensus eurkaryotic initiation site, CCGCCATGC (Kozak, 1984, Nuc. Acid. Res. 12: 857–872). No putative polyadenylation sequence is contained in the 3' non-coding region, however, it does contain two closely spaced ATAAA motifs which may function as a polyadenylation signal.

Biochemical Characterization of the Human L6 Antigen

L6 antigen produced by transfected COS cells was examined by immunoprecipitation. Transfected COS cells were surface labeled with $^{125}I$ by the lactoperoxidase method, and were then extracted with PBS containing 1% CHAPS 5 mM EDTA, 0.5 mM phenylmethylsulfonylfluoride (PMSF), 8 µg/ml aprotinin and 2 µg/ml leupinin for thirty minutes at 4° C. Following centrifugation at 13,000× g, the supernatant was made 5% in bile salts (sodium cholate/deoxycholate) and extracted for an additional 30 minutes. After centrifugation at 100,000× g for 30 minutes, the supernatant was precleared with Protein A Sepharose. Immunoprecipitations were performed with chimeric L6 or a control antibody (chimeric 96.5) at a concentration of 40 µg/ml monoclonal antibody. Immune complexes were collected on Protein A Sepharose (Repligen) and washed four times with PBS. Samples were heated in sample buffer containing 2% SDS and 5% beta-mercaptoethanol. Polyacrylamide gel electrophoresis was carried out on 14% SDS gels and iodinated proteins were detected by autoradiography. Immune precipitations were carried out on the L6 antigen-negative melanoma cell line H3606 as an additional control.

Figure 3:
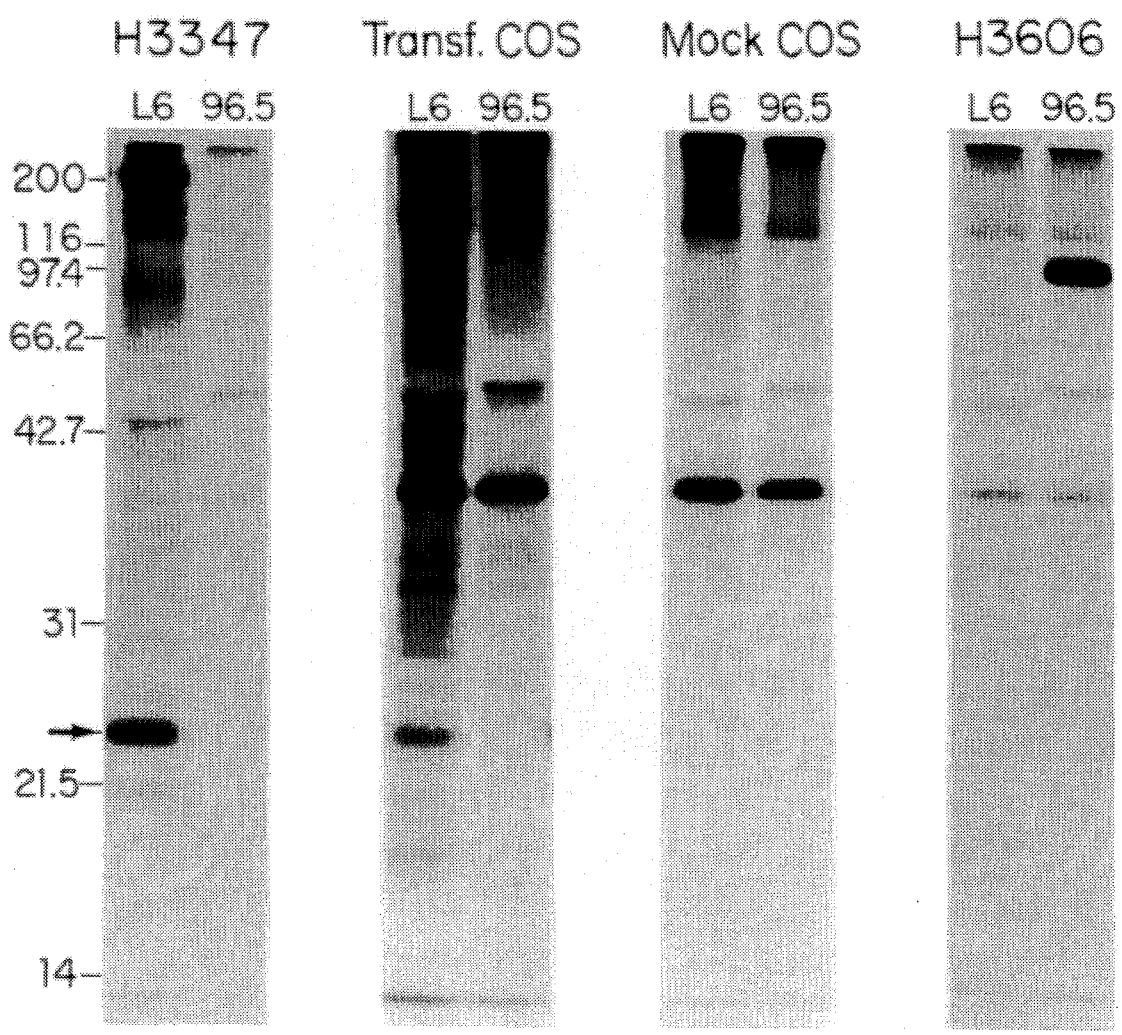
FIG. 3: Radioimmune precipitation analysis to determine the presence of L6 antigen in various cells including COS cell transfected with cDNA encoding the L6 antigen. Radiolabeled cell surface proteins from the colon carcinoma H3347, L6 transfected COS cells, mock transfected COS cells and the melanoma H3606 were immunoprecipitated with either an anti-L6 monoclonal antibody (L6) or an isotype matched control monoclonal antibody (96.5) and analyzed by SDS-PAGE. The location of the putative L6 antigen is indicated by an arrow.

Results of the immune precipitations of transfected COS cells, mock transfected COS cells, L6 antigen-positive H3347 cells and L6 antigen-negative H3606 are seen in FIG. 3. A specific band reactive with chimeric L6 antibody of about 24 kDa is only present in transfected COS cells and L6 antigen positive H3347 cells. The band is not brought down in precipitations with negative control antibody chimeric 96.5. A second band with a molecular mass of approximately 220 kDa was also immunoprecipitated by the L6 monoclonal antibody from H3347 tumor cells, but not from other cells. The 220 kDa protein is consistently precipitated from the L6 positive tumor cell lines H3347, A549 and H3477 (data not shown). High performance liquid chromatography (HPLC) of solubilized L6 antigen shows three peaks of reactivity with apparent molecular masses of 230, 500 and 670 kDa (data not shown). These results, in combination with the immunoprecipitation data, suggests that the 24 kDa L6 antigen does not exist in a monodisperse form, but is present in higher molecular weight complexes in tumor cells. It is possibly these molecular associations that have made the L6 antigen so difficult to characterize using other standard biochemical separation techniques.

EXAMPLE 3

RNA and DNA Analysis of Cancer Cell Lines

This example examines RNA and DNA isolated from various cancer cell lines for the presence of sequences which encode the L6 antigen. Cell lines were used which had previously been shown to be reactive or non-reactive with the monoclonal antibody L6. In all cases examined, levels of L6-related mRNA correlated well with levels of L6 antigen expression on the cell surface.

Total RNA was prepared from $1\times10^7$ cells of the ovarian (H3639), colon (H3719 and H3347) and lung (H2981 and A549) carcinoma cell lines, melanoma cell lines H3606 and A375, the T cell line Jurkat B cell line Ramos and myeloid cell line TPH1 by the guanidinium thiocyanate method. Equal amounts of RNA (10 μg) were loaded onto a 1% agarose/formaldehyde gel after denaturation for size separation. The RNA was transferred to a Zeta-Probe nylon membrane (BioRad) and a radiolabeled single stranded CDM8/L6 DNA was used as a probe as previously described (Seed and Aruffo, 1987, Proc. Natl. Acad. Sci. USA 84: 3365–3349). The membrane was washed in 40 mM sodium phosphate (pH 7.8), and exposed to x-ray film.

Figure 4:
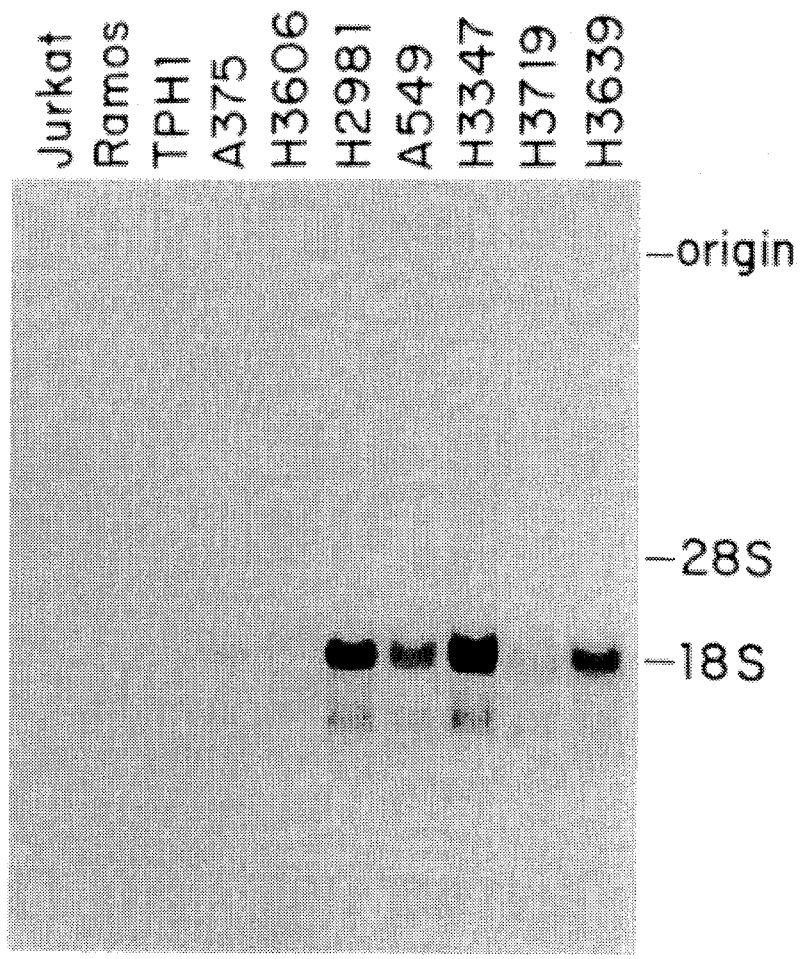
FIG. 4: RNA blot analysis was carried out on various cell lines to determine if mRNA for the L6 antigen is produced by the cell lines. Total RNA was prepared from the lung carcinoma cell lines H2981 and A549, the ovarian carcinoma cell line H3637, the colon carcinoma cell lines H3719 and H3347, the melanoma cell lines H3606 and A375, the T cell line Jurkat, the B cell line Ramos, and the myeloid cell line TPH1. Radiolabeled cDNA encoding the L6 antigen was used as the probe. The position of the 18s and 28s fibosomal RNAs are indicated on the right.

Two RNA species with molecular sizes of about 1.8 and 1.2 kb were visible in RNA derived from the lung carcinoma cell lines H2981 and A549 the ovarian carcinoma cell line H3637, and the colon carcinoma cell lines H3719 and H3347 (FIG. 4). These two bands were also weakly visible on L6 antigen on its surface, as determined by binding of the L6 monoclonal antibody. No hybridizing messages were seen in RNA isolated from the melanoma cell line H3606, the T cell line Jurkat, the B cell line Ramos, and the myeloid cell line TPH1. In all cases examined, the levels of L6-431ated in mRNA has correlated well with the levels of L6 antigen expression on the cell surface is determined by monoclonal antibody binding.

The presence of genomic DNA encoding L6 antigen was also determined. Genomic DNA was obtained from $1\times10^8$ cells from lung carcinoma cell line A549, melanoma cell line H3606, and human endothelial cells (passage 4) as described by Seed and Aruffo, supra. Equal amounts of DNA (15 μg) were digested with the restriction enzymes Eco RI, Hind III, Pvu II, and Xba I, as recommended by the vendor and loaded onto a 0.8% agarose gel for size separation. After separation the DNA was transferred onto a Zeta-Probe nylon membrane and CDM8/L6 DNA was used as the probe as described above.

Blot hybridization analysis of genomic DNA isolated from lung carcinoma cell line A549, melanoma cell line H3606 and human endothelial cells gave identical patterns after digestion with the restriction enzymes Eco RI, Hind III, Pvu II, and XbaI (data not shown). These results suggest that gross genomic rearrangements are not involved in the abnormal expression of the L6 antigen in carcinomas.

EXAMPLE 4

Glycosylation of the L6 Antigen

In this example the L6 antigen was expressed in vitro both in the presence of membrane and without. The amount and type of glycosylation was determined on the expressed antigen by digestion with either and N-glycanase or O-glycanase. A protein product was produced by in vitro transcription and translation of L6 antigen cDNA similar in size to that expressed by COS cells transfected with the same cDNA. Immunoprecipitation analysis of the translation products with chimeric L6 antibody revealed that the product of the cDNA was not recognized by the antibody when it was produced in the absence of membranes. However, when treated with glycanase the protein produced in the presence of membranes were stripped of their carbohydrates and they were still immunoprecipitated by the antibody indicating the membrane and/or appropriate glycosylation may be required in order for the molecule to assume a confirmation necessary for antibody recognition and binding.

In Vitro Transcription and Translation of the L6 Antigen

Ten micrograms of CDM8 plasmid DNA containing L6 antigen cDNA was linearized with Pst I, which cuts immediately 3' of the insert. After phenol extraction and ethanol precipitation, mRNA was synthesized from 3 μg of DNA using the mCAP mRNA capping kit (Stratagene, La Jolla, Calif.) containing $m^7GppG$ according to manufacturer's instructions.

The in vitro transcribed mRNA was treated with DNase I, then phenol extracted and precipitated with ethanol. The RNA concentration was estimated by agarose gel electrophoresis.

Approximately 1 μg of L6 antigen mRNA was translated in 50 μl reactions using nuclease treated rabbit reticulocyte lysate and a cysteine-minus amino acid mixture (Promega, Madison, Wis.). The translation was performed in the presence of $^{35}S$-cysteine at 30° C. as recommended by the manufacturer. Where indicated, four equivalents of canine microsomal membranes (Promega) were included in the translation reaction.

Glycosidase Digestion

In vitro translated products were digested with either N-glycanase, O-glycanase plus neuraminidase, or subjected to a mock digestion.

A sample of translation product was incubated at 37° C. for 36 hours in 4.5 U N-glycanase (Genzyme, Cambridge, Mass.) in 25 mM sodium phosphate, pH 7.5, 0.5% CHAPS, 5 EDTA, 0.01% sodium azide, 35 μg/ml leupeptin and 30 μg/ml aprotinin. The mock digestion was performed under identical conditions except that N-glycanase was omitted. For digestion with O-glycanase plus neuraminidase, a sample was incubated at 37° C. for 36 hours in 20 mU O-glycanase (Genzyme), 0.1 U neuraminidase (benzyme), 25 mM sodium phosphate, pH 7.0, 0.5% CHAPS, 0.01% sodium azide, 35 μg/ml leupeptin and 30 μg/ml aprotinin.

Immunoprecipitation

In vitro translated products, glycanase treated or untreated were diluted 8-fold in immunoprecipitation buffer (PBS, 5% bile salts (sodium cholate/deoxycholate), 5 mM EDTA, 0.5M phenylmethylsulfonyl fluoride, 8 μg/ml aprotinin and 2 μg/ml leupeptin). Immunoprecipitations were performed with 40 μg/ml chimeric L6 for 2 hours on ice. Immune complexes were collected on Protein A Sepharose (Repligen, Cambridge, Mass.). for one hour at 4° C. and washed four times with immunoprecipitation buffer followed by two washes with PBS. Samples were boiled in sample buffer containing 2% SDS and 5% 2-mercaptoethanol prior to separation by SDS-polyacrylamide electrophoresis on 15% gels. The gels were treated with Intensity autoradiography enhance (Dupont) and $^{35}S$-labeled proteins were detected by autoradiography.

In vitro transcription and translation of the cDNA in the absence of membranes as shown in FIG. 5 resulted in the appearance of a 22 kDa protein product predicted by the open reading frame. The addition of microsomal membranes to the translation reaction, which can allow for potential glycosylation and membrane insertion, resulted in an increase in the apparent molecular weight of the product to 24–25 kDa (FIG. 5B, lane 4). This is the same size molecule as observed in immunoprecipitations with the monoclonal antibody L6 from $^{125}I$-surface labeled tumor cells or COS cell transfected with the cDNA. Treatment of this product with N-glycanase, (which completely removes N-linked oligosaccharides) but not O-glycanase and neuraminidase, reduced the apparent molecular weight back to 22 kDa, indicating that N-linked carbohydrate addition does occur for at least one of the two potential glycosylation sites predicted from the cDNA sequence.

Immunoprecipitation analysis of the in vitro translation products with chimeric L6 antibody revealed that the product of the cDNA was not recognized by the antibody when it was produced in the absence of membranes. However, both the 24–25 kDa product, and the 22 kDa protein stripped of its carbohydrate were immunoprecipitated from translation reactions performed in the presence of membranes. Thus, the protein must require association with membrane and/or appropriate glycosylation in order to assume the conformation necessary to form the epitope recognized by L6, but once formed, the presence of carbohydrate is not required for antibody binding.

---

We claim:

1. A purified oligonucleotide sequence encoding a polypeptide having the contiguous sequence of amino acid residues depicted in Sequence I.D. No. 2.

2. An oligonucleotide sequence wherein the nucleotide sequence consists of the nucleotide sequence depicted in Sequence I.D. No. 1 from bp 109 to bp 715.

3. A recombinant plasmid or vector comprising an oligonucleotide sequence encoding the polypeptide having the contiguous sequence of amino acid residues depicted in Sequence I.D. No. 2.

4. A host cell transformed or transfected with a plasmid or vector of claim 3.

5. A host cell of claim 4, wherein the host cell is selected from the group consisting of a COS cell line and a chinese hamster ovary cell line.

6. A method for the expression of the oligonucleotide sequence encoding the polypeptide containing the contiguous sequence of amino acid residues depicted in Sequence I.D. No. 2 comprising:

(a) inserting a nucleotide sequence encoding the contiguous sequence of amino acid residues depicted in Sequence I.D. No. 2 into an appropriate vector to form an expression vector;

(b) inserting the expression vector into a suitable host cell;

(c) culturing the host cell; and (d) purifying the expressed polypeptide produced by the host cell.

7. A recombinant plasmid or vector comprising an oligonucleotide sequence consisting of the nucleotide sequence depicted in Sequence I.D. No. 1 from bp 109 to bp 715.

8. The recombinant plasmid or vector of claim 3, wherein the oligonucleotide sequence is operably linked to control sequences compatible with a prokaryotic host.

9. The recombinant plasmid or vector of claim 3, wherein the oligonucleotide sequence is operably linked to control sequences compatible with a eukaryotic host.

10. The recombinant plasmid or vector of claim 3, wherein the oligonucleotide sequence is operably linked to control sequences compatible with a mammalian host.

11. Bacterial cells transformed with the recombinant vector of claim 8.

12. Eukaryotic cells transformed with the recombinant vector of claim 9.

13. Mammalian cells transformed with the recombinant vector of claim 10.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1188 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens
        ( F ) TISSUE TYPE: Colon
        ( G ) CELL TYPE: Carcinoma
        ( H ) CELL LINE: H3347

( x i ) SEQUENCE DESCRIPTION: SEQ ID NO:1:

```
TCGAGATCCA  TTGTGCTCTA  AAGGCTCGCC  CTCCTGTGCA  TCGCGGCTAA  TTTGGGGTAT     60
CACTGAGCTG  AAGACAAAGA  GAAGGGGGAG  AAAACCTAGC  AGACCACCAT  GTGCTATGGG    120
AAGTGTGCAC  GATGCATCGG  ACATTCTCTG  GTGGGGCTCG  CCCTCCTGTG  CATCGCGGCT    180
AATATTTTGC  TTTACTTTCC  CAATGGGGAA  ACAAAGTATG  CCTCCGAAAA  CCACCTCAGC    240
CGCTTCGTGT  GGTTCTTTTC  TGGCATCGTA  GGAGGTGGCC  TGCTGATGCT  CCTGCCAGCA    300
TTTGTCTTCA  TTGGGCTGGA  ACAGGATGAC  TGCTGTGGCT  GCTGTGGCCA  TGAAAACTGT    360
GGCAAACGAT  GTGCGATGCT  TTCTTCTGTA  TTGGCTGCTC  TCATTGGAAT  TGCAGGATCT    420
GGCTACTGTG  TCATTGTGGC  AGCCCTTGGC  TTAGCAGAAG  GACCACTATG  TCTTGATTCC    480
CTCGGCCAGT  GGAACTACAC  CTTTGCCAGC  ACCGAGGGCC  AGTACCTTCT  GGATACCTCC    540
ACATGGTCCG  AGTGCACTGA  ACCCAAGCAC  ATTGTGGAAT  GGAATGTATC  TCTGTTTTCT    600
ATCCTCTTGG  CTCTTGGTGG  AATTGAATTC  ATCTTGTGTC  TTATTCAAGT  AATAAATGGA    660
GTGCTTGGAG  GCATATGTGG  CTTTTGCTGC  TCTCACCAAC  AGCAATATGA  CTGCTAAAAG    720
AACCAACCCA  GGACAGAGCC  ACAATCTTCC  TCTATTTCAT  TGTAATTTAT  ATATTTCACT    780
TGTATTCATT  TGTAAAACTT  TGTATTAGTG  TAACATACTC  CCCACAGTCT  ACTTTTACAA    840
ACGCCTGTAA  AGACTGGCAT  CTTCACAGGA  TGTCAGTGTT  TAAATTTAGT  AAACTTCTTT    900
TTTGTTTGTT  TATTTGTGTA  ACATACTCCC  CACAGTCTAC  TTTTACAAAC  GCCTGTAAAG    960
ACTGGCATCT  TCACAGGATG  TCAGTGTTTA  AATTTAGTAA  ACTTCTTTTT  TGTTTGTTTA   1020
TTTGTTTTTG  TTTTTTTTTA  AGGAATGAGG  AAACAAACCA  CCCTCTGGGG  GTAGTTTACA   1080
GACTGAGTGA  CAGTACTCAG  TATATCTGAG  ATAAACTCTA  TAATGTTTTG  GATAAAAATA   1140
ACATTCCATG  GCACATATAT  ACAATAGTGA  TTGGCTTTAG  AGCACAAT               1188
```

(2) INFORMATION FOR SEQ ID NO:2:

(i) SEQUENCE CHARACTERISTICS:
        (A) LENGTH: 202 amino acids
        (B) TYPE: amino acid
        (D) TOPOLOGY: linear (ii) MOLECULE TYPE: protein (v) FRAGMENT TYPE: N-terminal (vi) ORIGINAL SOURCE:
        (A) ORGANISM: Homo sapiens
        (F) TISSUE TYPE: Colon
        (G) CELL TYPE: carcinoma
        (H) CELL LINE: H3347

(xi) SEQUENCE DESCRIPTION: SEQ ID NO:2:

| Met 1 | Cys | Tyr | Gly | Lys 5 | Cys | Ala | Arg | Cys | Ile 10 | Gly | His | Ser | Leu | Val 15 | Gly |
|---|---|---|---|---|---|---|---|---|---|---|---|---|---|---|---|
| Leu | Ala | Leu | Leu 20 | Cys | Ile | Ala | Ala | Asn 25 | Ile | Leu | Leu | Tyr | Phe 30 | Pro | Asn |
| Gly | Glu | Thr 35 | Lys | Tyr | Ala | Ser | Glu 40 | Asn | His | Leu | Ser | Arg 45 | Phe | Val | Trp |
| Phe | Phe 50 | Ser | Gly | Ile | Val | Gly 55 | Gly | Gly | Leu | Leu | Met 60 | Leu | Leu | Pro | Ala |
| Phe 65 | Val | Phe | Ile | Gly | Leu 70 | Glu | Gln | Asp | Asp | Cys 75 | Cys | Gly | Cys | Cys | Gly 80 |
| His | Glu | Asn | Cys | Gly 85 | Lys | Arg | Cys | Ala | Met 90 | Leu | Ser | Ser | Val | Leu 95 | Ala |
| Ala | Leu | Ile | Gly 100 | Ile | Ala | Gly | Ser | Gly 105 | Tyr | Cys | Val | Ile | Val 110 | Ala | Ala |
| Leu | Gly | Leu 115 | Ala | Glu | Gly | Pro | Leu 120 | Cys | Leu | Asp | Ser | Leu 125 | Gly | Gln | Trp |
| Asn | Tyr 130 | Thr | Phe | Ala | Ser | Thr 135 | Glu | Gly | Gln | Tyr | Leu 140 | Leu | Asp | Thr | Ser |
| Thr 145 | Trp | Ser | Glu | Cys | Thr 150 | Glu | Pro | Lys | His | Ile 155 | Val | Glu | Trp | Asn | Val 160 |
| Ser | Leu | Phe | Ser | Ile 165 | Leu | Leu | Ala | Leu | Gly 170 | Gly | Ile | Glu | Phe 175 | Ile | Leu |
| Cys | Leu | Ile | Gln 180 | Val | Ile | Asn | Gly | Val 185 | Leu | Gly | Gly | Ile | Cys 190 | Gly | Phe |
| Cys | Cys | Ser 195 | His | Gln | Gln | Gln | Tyr 200 | Asp | Cys | | | | | | |